(12) United States Patent
Bluemler et al.

(10) Patent No.: US 9,189,597 B2
(45) Date of Patent: Nov. 17, 2015

(54) TECHNICAL MEDICAL DEVICE HAVING A TOUCHSCREEN AND METHOD

(75) Inventors: Holger Bluemler, Karben (DE); Wolfgang Wehmeyer, Tuebingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 551 days.

(21) Appl. No.: 13/396,100

(22) Filed: Feb. 14, 2012

(65) Prior Publication Data

US 2012/0212434 A1 Aug. 23, 2012

Related U.S. Application Data

(60) Provisional application No. 61/444,316, filed on Feb. 18, 2011.

(30) Foreign Application Priority Data

Feb. 18, 2011 (DE) .......................... 10 2011 011 769

(51) Int. Cl.
| | |
|---|---|
| G06F 3/033 | (2013.01) |
| G06F 19/00 | (2011.01) |
| A61M 1/14 | (2006.01) |
| G06F 3/041 | (2006.01) |

(52) U.S. Cl.
CPC ............. *G06F 19/3406* (2013.01); *A61M 1/14* (2013.01); *G06F 3/041* (2013.01); *G06F 3/0414* (2013.01); *G06F 3/0418* (2013.01); *A61M 2205/505* (2013.01); *G06F 19/3481* (2013.01); *G06F 2203/04106* (2013.01)

(58) Field of Classification Search
CPC .................. G06F 2203/04106; G06F 19/3481; G06F 3/041; G06F 3/0418; G06F 3/0414; G06F 19/3406; A61M 2205/505; A61M 1/14
USPC ......................... 345/173; 178/18.01; 463/30
See application file for complete search history.

(56) References Cited

U.S. PATENT DOCUMENTS

| | | | |
|---|---|---|---|
| 5,818,429 A | 10/1998 | Tanaka et al. | |
| 6,063,030 A | * 5/2000 | Vara et al. ...................... | 600/437 |

(Continued)

FOREIGN PATENT DOCUMENTS

| | | |
|---|---|---|
| CN | 1157434 | 8/1997 |
| CN | 1596413 | 3/2005 |

(Continued)

OTHER PUBLICATIONS

"Touch-Screen mit Piezo-Aktor zur taktilen RA 1/4 ckmeldung"IP. Com Inc., Feb. 17, 2011 (translation attached).

*Primary Examiner* — Abbas Abdulselam
(74) *Attorney, Agent, or Firm* — Jacobson Holman, PLLC.

(57) ABSTRACT

A medical device is configured such that operator inputs are more convenient and more reliable via a touchscreen display. The medical device includes a touchscreen having two redundant finger-position sensors. At least one of the sensors has additional piezoelectric elements, which can modify at least partial areas of the touchscreen such that the sensors are differentiated from their surrounding areas by an elevation, a recess, a vibration or a change in the surface roughness sensed. A control unit differentiates intentional and unintentional operating entries, and in the event of failure of the visual display device of the touchscreen display ensures at least a restricted operability of the touchscreen display.

19 Claims, 6 Drawing Sheets

(56) References Cited

U.S. PATENT DOCUMENTS

| | | | |
|---|---|---|---|
| 6,676,621 B1 | 1/2004 | Menninger | |
| 6,825,833 B2 | 11/2004 | Mulligan et al. | |
| 7,935,250 B2 * | 5/2011 | Castellano et al. | 210/143 |
| 8,243,031 B2 * | 8/2012 | Kumamoto | 345/173 |
| 8,704,799 B2 | 4/2014 | Frey et al. | |
| 8,730,181 B1 * | 5/2014 | Raman et al. | 345/173 |
| 2007/0235376 A1 | 10/2007 | Daniel | |
| 2008/0100587 A1 * | 5/2008 | Sano et al. | 345/173 |
| 2009/0183147 A1 * | 7/2009 | Davis et al. | 717/168 |
| 2009/0250268 A1 | 10/2009 | Staton et al. | |
| 2009/0294339 A1 | 12/2009 | Biewer et al. | |
| 2010/0005416 A1 | 1/2010 | Hedmann et al. | |
| 2010/0066686 A1 | 3/2010 | Joguet et al. | |
| 2010/0148993 A1 | 6/2010 | Lee | |
| 2011/0291975 A1 | 12/2011 | Dietz et al. | |

FOREIGN PATENT DOCUMENTS

| | | |
|---|---|---|
| CN | 1795019 | 6/2006 |
| CN | 101512467 | 8/2009 |
| CN | 1020167868 | 4/2011 |
| DE | 19849787 | 2/2000 |
| DE | 10 2007 039 609 | 2/2009 |
| DE | 10 2008 031 660 | 1/2010 |
| DE | 102008058568 | 5/2010 |
| WO | 2008/030594 | 3/2008 |
| WO | WO 2009/085060 | 7/2009 |
| WO | WO 2010/105705 | 9/2010 |

* cited by examiner

TECHNICAL MEDICAL DEVICE HAVING A TOUCHSCREEN AND METHOD

CROSS-REFERENCE TO RELATED APPLICATIONS

This application claims the benefit of US provisional application No. 61/444,316, filed Feb. 18, 2011, and claims the priority of German number 10 2011 011 769.5, filed Feb. 18, 2011, hereby incorporated by reference.

BACKGROUND OF THE INVENTION

1. Field of Invention

The invention relates to a technical medical device, in particular a blood treatment device having at least one touchscreen and a method for display and input of information in a blood treatment device having at least one touchscreen.

2. Description of the Prior Art

Technical medical devices with touch-sensitive displays (touchscreens) as a means for simultaneously displaying information and receiving operator input are widely known in the state of the art. One example of such a technical medical device is the Hemodialysis Machine 5008 from Fresenius Medical Care.

Technical medical devices having touchscreens offer the user a convenient, variable and hygienic user interface due to the flat unbroken surface.

Touchscreens for technical medical devices have so far offered essentially only smooth flat surfaces. The operator recognizes the area of the display where a fingerprint is expected based on visual display of a control panel. There is no tactile acknowledgement of whether the expected area has been touched. Such tactile feedback is offered by conventional mechanical switches with which operation requires a tangible application of force and/or with which operation can be sensed by the actuator travel. One disadvantage of such mechanical switches due to their design is their property of frequently breaking through the surface of the technical medical device, which makes hygienic cleaning of the surface difficult. In addition, mechanical switches do not offer the variability of a software-controlled switching matrix of a touchscreen, which offers flexibility with regard to varying the number, size and position of the virtual switches on the touchscreen.

For the safety of a technical medical device, it is essential for the input and display of information on a touchscreen display to function reliably and unambiguously.

For this purpose, it is advisable to have a redundant design of the input option via the touchscreen by providing another input option for important information in the event of failure of the input functionality of the touchscreen, for example, for safe termination of a patient's treatment. In the state of the art, this is made possible by additional mechanical switches or buttons, for example. The properties mentioned above with regard to mechanical switches have proven to be a disadvantage in this regard.

Devices having a touchscreen with tactile feedback are known from the field of telecommunications and computer technology. WO2009/085060 describes one such device.

Tactile feedback is obtained with such devices in order to impart the feeling of a mechanical button to the user when he applies his finger to the touchscreen display. This constitutes a gain in convenience in particular when the device has no mechanical keypad but instead has only a touchscreen such as that on various mobile telephones or minicomputers. In these applications, convenience of use is the primary concern, but technical safety advantages are not achieved by a touchscreen having tactile feedback with the known devices.

However, the safety aspect is of primary concern with technical medical devices.

SUMMARY OF THE INVENTION

The object of the present invention is therefore to improve upon a technical medical device having a touchscreen in such a way that the safety of the technical medical device and operating convenience are increased.

These objects are achieved according to the invention by the various embodiments of a device and a method having the features described herein.

Tactile signals are understood to be deformations, i.e., permanent or alternating changes in the extent of something.

The present invention is based on a technical medical device, in particular a dialysis machine, having at least one touchscreen, whereby the touchscreen has two redundant sensors for detecting the position of a finger pressing on the touchscreen.

In addition, the invention is based on a method for display and input of information on a technical medical device having a touchscreen with at least two redundant sensors, where the position of a fingerprint on the display screen is determined by both sensors.

Furthermore, the invention is based on a method for display on a technical medical device having at least one touchscreen, where tactile signals are generated on the touchscreen.

In a preferred embodiment of the invention, at least one of the sensors of the touchscreen with which the position of a fingerprint on the touchscreen is determined comprises a plurality of piezoelectric elements.

Piezoelectric elements make use of the piezoelectric effect to execute a movement either by applying an electrical voltage or to generate an electrical voltage by the application of a force. Piezoelectric elements can thus be equipped as both force sensors and actuators. Piezoelectric elements may be certain crystals (piezoelectric crystals) or piezoelectric ceramics, i.e., polycrystalline materials.

The piezoelectric elements may be distributed over the touchscreen surface in a matrix pattern and can be controlled individually with local resolution by appropriate controls.

The piezoelectric elements may also be connected to the display in a force-locked manner at the corners or at the sides beneath the display.

In an alternative embodiment, the piezoelectric elements may also be arranged in larger numbers in certain positions of the display and may be present in reduced numbers or not at all at certain other positions. Thus an improved resolution of the tactile signal can be achieved at certain positions on the touchscreen without increasing the total number of piezoelectric elements.

In one embodiment, the piezoelectric elements are formed by contacting an essentially light-permeable piezoelectric layer on opposite sides of electrodes that are essentially light-permeable. In this way, a plurality of electrodes on the surface and on the bottom side of the piezoelectric layer preferably runs orthogonally to one another at regular intervals, especially over the entire display.

In the view from above, a piezoelectric element is formed as an intersection of an electrode running on the surface of the piezoelectric layer with an electrode running on its bottom side and the piezoelectric material situated in between.

The electrodes situated at the top in relation to the piezoelectric layer form a pattern of lines, preferably of equal width, which are equidistant from and parallel to one another with a spacing that preferably corresponds to the line width. The electrodes situated at the bottom in relation to the piezoelectric layer are also arranged similarly. As seen from above, both electrode levels have a uniform grid, with any intersection of electrodes running over and under the piezoelectric layer, forming a piezoelectric element that can be controlled and/or read out individually.

Multiplying the number of electrodes on the top side of the piezoelectric layer times the number of electrodes on the bottom side of the piezoelectric layer yields the number of piezoelectric elements.

A certain piezoelectric element can be controlled and/or read out by selecting one electrode on the top side of the piezoelectric layer and one electrode on the bottom side. By applying a voltage difference to an electrode on the top side and to an electrode on the bottom side of the piezoelectric layer, the piezoelectric material between these two electrodes is excited to deformation.

In the same way, the voltage drop across a piezoelectric element can be picked up at the electrodes contacting this piezoelectric element.

In this embodiment, it has proven to be a disadvantage that the individual piezoelectric elements cannot be controlled and/or read out simultaneously independently of one another. A single electrode determines the potential of a plurality of piezoelectric elements on one side.

In an especially preferred embodiment, a plurality of light-permeable electrodes, preferably designed with a cuboid shape, is therefore arranged on the top side of the piezoelectric layer. Each of these electrodes can be controlled and read out by its own control line. The bottom side of the piezoelectric layer has a single light-permeable electrode, which runs over the entire surface of the piezoelectric light-permeable layer and whose potential can be controlled and read out by a single control line. In this embodiment, a piezoelectric element is formed between an electrode on the top side of the piezoelectric layer and the shared electrode on the bottom side of the piezoelectric layer. This embodiment enables individual and simultaneous controllability and readability of each individual piezoelectric element.

The surface of the electrodes on the top side of the piezoelectric layer may be based on the touch surface of a human finger (approximately 1 $cm^2$). It is also possible to design the electrodes at the top side of the piezoelectric layer individually in shape and size to be adapted to a preferred visual display, for example. A large operating surface, which always appears at a certain location on the touchscreen (for example, "enter") may be covered by a single larger piezoelectric element accordingly, whereas smaller electrodes are present at other locations.

Natural crystals such as berlinite, cane sugar, quartz, Rochelle salt, topaz or tourmalines, synthetic crystals such as gallium orthophosphate or langasite, ceramics or polymers may be used as the material for the piezoelectric elements. Essentially any material that deforms when a voltage is applied may be used for this purpose.

The electrodes may be made of a metal or a semiconductor, but are preferably designed as indium tin oxide (ITO) electrodes, which are largely transparent for visible light.

Embodiments of the touchscreen having tactile feedback are described below on the example of a dialysis machine. It will be clear to those skilled in the art that the embodiments described here can be applied to any technical medical device without restriction.

In one embodiment, the device is designed to read out the voltage of each piezoelectric element generated by the application of pressure. The piezoelectric elements in this embodiment operate like force sensors. The pressure of a finger on a corresponding location of the touchscreen is detected in this way. It may happen that the property of the touchscreen of detecting touch with position resolution is restricted or is no longer present, for example, due to a technical defect. In this case, an alternative redundant option in addition to the device that is present anyway may also be created by readout of the voltages of the piezoelectric elements which are generated by the pressure of a finger may create the possibility of detecting user input with position resolution.

It is conceivable that the signals of the device of the touchscreen which ascertain the position of the finger on the touchscreen (hereinafter referred to as the touchscreen finger sensor) may be compared with the corresponding voltages of the piezoelectric elements each time a finger presses against the touchscreen to thereby check on the functionality of both sensor devices.

For example, it may happen that the functionality of the touchscreen to detect touch with position resolution is defective or restricted, but the functionality of the piezoelectric elements is retained. Then the piezoelectric elements to which the operator is applying force by finger pressure create an electrical voltage by pressing a finger on the inventive touchscreen. An analysis and control device, which compares the signals of the touchscreen finger sensor with the signals of the piezoelectric elements, in this case detects the lack of sensor signals of the touchscreen finger sensor and therefore infers the existence of a defect or an error case. Similarly, a defect in functionality and/or an error case involving the piezoelectric elements can be detected if the analysis and control device detects signals of the touchscreen finger sensor but no signals of the piezoelectric element matrix. In both cases, the analysis and control device can display the presence of a defect for the operator and/or provide this information to another control device of the dialysis machine. This display may be a control signal and/or a visual, tactile or acoustic signal. In the event of a defect, the control unit of the dialysis machine may take measures, for example, may terminate an ongoing dialysis treatment in a controlled manner or may continue it to the end and allow further treatment only after the defect has been eliminated.

The device and the method according to the invention thus offer additional security with dialysis machines in that they offer a redundant input option. This redundant input option allows much more flexible possibilities of input than redundant mechanical switches, the number and position of which cannot be altered during operation. Due to the flexibility of the touchscreen with its tactile feedback, the operability of the dialysis machine can be maintained to an unlimited extent even in the event of an error or defect. For the patient, this means a significant improvement in the case when the touchscreen finger sensor fails, because the operability of the dialysis machine can continue without restriction due to the redundant input option. Thus it is not absolutely necessary to interrupt an ongoing dialysis treatment, which thereby increases convenience and security.

In another embodiment, the piezoelectric element matrix may also be utilized to detect the pressure of multiple fingers simultaneously. In the state of the art, touchscreens having a multitouch functionality are known, based on a special capacitive touchscreen technology.

With conventional capacitive touchscreen displays, when the user's finger approaches the display surface, it forms a capacitance with a coating (for example, of ITO) on the touchscreen; this coating is essentially transparent for visible light. A scratch-proof film or a glass cover is usually applied over the conductive coating in order to protect the coating from wear and make the touchscreen robust. This film or glass cover then functions as a dielectric for the plate capacitor thereby formed, whose one plate represents the conductive coating and whose other plate is formed by the approaching or applied finger. It is therefore essential for the function of capacitive touchscreens that the object touching the screen must be able to take up a charge, which is the case with a human finger. The corners of the conductive coating are connected to a.c. voltage sources. On touching the touchscreen, currents flow from these a.c. voltage sources over the conductive layer and the capacitor, which is formed by the finger and the conductive layer. The path from the respective a.c. voltage source to the point of contact of the finger then forms an electrical resistance here, the size of which depends on the specific conductivity of the coating and the length of the path. This yields current levels which are proportional to the length of the path; these current levels are detected by an analysis circuit and can be allocated to the instantaneous position of the finger.

This widespread and inexpensive design of capacitive touchscreens is unable to ascertain the positions of two fingers touching it because the current signals at two contact points cannot be allocated unambiguously to the positions of touch. Although touchscreens having a multitouch functionality are known from the state of the art, conventional dialysis machines are not equipped with touchscreens having a multitouch functionality.

Due to the additional piezoelectric element layer, such a functionality can also be implemented. Since each piezoelectric element can be queried individually, pressing with the fingers on different piezoelectric elements at the same time can also be detected. This can be used to span an interval of values on a value scale, for example, using two fingers in order to conveniently enter the upper and lower limits of a parameter, for example. It is also conceivable that, with the movement of two fingers on the touchscreen, an enlarged or reduced representation of the touchscreen display may be triggered beneath the movement of the fingers.

In another embodiment, the piezoelectric elements are designed to execute a movement, preferably at a right angle to the surface of the touchscreen, by applying an electrical control voltage. The electrical control voltage may be variable over time or may be the same for a period of time.

According to the invention, parts of the touchscreen may thereby be varied individually in their tactile properties. The changes comprise essentially recesses or elevations in partial areas of the touchscreen in comparison with the surrounding areas, vibration of partial areas and a change in roughness (smooth/rough) of partial areas of the touchscreen in comparison with surrounding areas. All the changes in tactile properties affecting partial areas of the touchscreen can also be applied to the total area of the touchscreen with an appropriate design of the inventive device and the inventive method.

For example, an electrical d.c. voltage may be applied to one or more piezoelectric elements of the matrix, whereupon the piezoelectric elements are lengthened or shortened in one dimension (depending on the polarity of the applied d.c. voltage) and this effect continues as long as the d.c. voltage is being applied. This shortening or lengthening of one or more piezoelectric elements is sensed as a recess or elevation by a user whose finger is resting on the location above the respective piezoelectric elements.

In this way, a location on the touchscreen such as an input field, which appears as an elevated area for contact with respect to the surrounding area, may be created on the touchscreen. A partial area of the touchscreen, which leads to unambiguous input of information when touched by an operator, may be defined as the input field.

For example, a 10-key keypad can be represented visually. The impression of a mechanical key can thus be created by elevated locations over the respective numeral indicated, while the dividing lines between the input fields are not otherwise elevated.

To support the tactile effect and to simulate mechanical keys or switches, it is possible that, after the user's finger comes in contact with an elevated input field, which is detected by the sensors of the touchscreen, the analysis and control device may control the piezoelectric elements forming this input field in such a way that they then form a recess or a planar surface. For this purpose, the controlling voltage of the corresponding piezoelectric elements is reversed or stopped after the contact is detected. This reversal in polarity or stopping of the control voltage may take place suddenly or may proceed more slowly.

It is also conceivable for the voltage over the piezoelectric elements to also be monitored in the controlled state. Thus the application of a mechanical force due to the pressure of a finger can be detected. The greater the pressure of the finger on the piezoelectric element, the greater is the modulation of the control voltage by the voltage generated by the piezoelectric element. In practice, a change in the d.c. voltage component of the control voltage due to a force acting on the piezoelectric element can be observed. In this embodiment, the piezoelectric elements operate as force sensors and as actuators at the same time.

This information can be used to differentiate between unintended touching of the touchscreen and intentional user input. In case of doubt, unintentional touching of the touchscreen will trigger a signal of the sensors of the touchscreen, whereas voltages over the respective piezoelectric elements of the operating field will not trigger a signal or will be modulated only slightly. Intentional touch occurs with a certain application of force by the finger of the user, which triggers a signal of the touchscreen sensors as well as causing a certain modulation of the voltages over the respective piezoelectric elements, which is greater than a previously defined limit value. When the limit value is exceeded, an intentional input is thus detected, after which the operating fields can change from an elevated state to a recessed state in the manner already described. This ensures that a certain application of force is necessary for a user input. Furthermore, this also simulates the behavior of mechanical switches or buttons more realistically.

The device and the methods according to the invention thus offer additional security with dialysis machines, in that they detect unintentional user input and prevent faulty operation.

In another embodiment of the invention, it is possible to provide for operability via the piezoelectric elements to be ensured even in the event of failure of the visual display of the touchscreen. For example, if it is found that the visual display of the touchscreen is defective, for example, due to a user input via a corresponding alternative input option, for example, a "display defective" button or by inquiry of suitable sensors, for example, light-sensitive components (photodiodes, photo-transistors, etc.), which monitor the background lighting of the display and in the event of a failure in the background lighting, transmit a corresponding message to the control unit, the piezoelectric elements can thus be controlled by the fact that they are used simultaneously as the input and output device.

In this case the display surface may be subdivided into multiple partial areas with differentiable tactile properties, for example, so that they can be differentiated from one another by a user/operator by tactile sensation. A certain action which is known to the user and/or documented by suitable means is assigned to each partial area. For example, a document may be present which shows which partial areas of the display are associated with which tactile property and which action is performed when this partial area is selected by pressing on it with a finger or the hand of the user. For example, it is possible to document that the touchscreen surface is subdivided into four parts, the position of which is characterized by corresponding tactile properties and/or positions on the touchscreen. For example, a partial area may be characterized with the tactile property "elevated" and "lower right" and the action "terminate dialysis treatment" may be assigned to this partial area. Another partial area may be characterized similarly with the tactile property "vibrating" and "upper left" and associated with the action "continue dialysis treatment." In the event of failure of the visual display of the touchscreen, it is thus possible to ensure at least limited operability of the dialysis machine in order to terminate the dialysis treatment safely, for example, or to continue it safely in the judgment of the person operating the machine (physician).

The inventive device and the inventive method thus offer an additional security with dialysis machines, in that they ensure at least reduced operability of the dialysis machine in the event of failure of the visual display of the touchscreen.

In another embodiment of the invention, it is possible to provide for only operating surfaces which are intended for user input to be elevated. For example, when entering numerical values, which may vary only within a certain interval, the input may be designed in such a way that only allowed operating fields, namely those assigned to plausible, i.e., allowed numbers, are elevated in the order of input of the numbers. For example, if an entry only within the interval of numbers from and including zero up to and including 50 is allowed, then when the first digit is entered, the operating fields with the numbers 0 to 5 are elevated, and when entering the second digit, the operating fields with the numbers 0 to 9 or only the number 0 (if the first digit was 5) is/are elevated. This tactile characterization of allowed operating fields can be supported by corresponding visual display and acoustic signals. Allowed operating fields may thus be displayed in a different color or intensity than unallowed operating fields, and an acoustic signal may be output in the event of a faulty input.

It is possible to provide that the operating fields not provided for input are recessed due to the piezoelectric elements.

Instead of that, it is possible to provide for the operating fields that are provided for input to be recessed by the piezoelectric elements and for the operating fields that are not intended for input to be elevated.

It is also possible to provide that by pressing a finger on operating fields not provided for input, these fields will vibrate to draw the operator's attention to the faulty input by tactile sensation.

This vibration is created by controlling the respective piezoelectric elements with an a.c. voltage, so that the piezoelectric elements vibrate with the frequency of the control voltage. The vibration rate is advantageously in the range of less than 100 Hz to more than 30 Hz in order to be detected by the operator as a vibration. A vibration at this frequency and at the possible amplitude, which is restricted due to the piezoelectric elements, and with the very small area available in practice, does not lead to an audible sound emission and therefore is only sensed.

In another embodiment, the piezoelectric elements may be controlled in such a way that they vibrate at a high frequency. Vibration at a high frequency, preferably in the range above 20 kHz, is perceived by the operator as a rough surface. At a vibration frequency of more than 20 kHz, it is advantageous that the sound emission associated with this vibration is not audible for humans. In this way, the operating surfaces of the touchscreen may be differentiated perceptibly from other surfaces or operating surfaces of the touchscreen.

Another embodiment relates to the use of at least three actuators, preferably four, in particular piezoelectric elements, which are situated on the edges or the corners beneath the touchscreen and support it there in a form-fitting manner. When designed in this way, the entire display can be moved by the actuators. Likewise, the pressure of a finger on the display can be detected by a query of the piezoelectric element voltage or alternative pressure sensors. An active force of the pressure of a finger on the display is distributed as a function of position to the force sensors situated at the edges or corners. By comparing the sensor signals, it is possible to determine the position and intensity of finger pressure.

All the controls and readout processes of the piezoelectric elements described above can also be combined with one another without restriction. For example, an elevated vibrating area can be implemented in that the corresponding piezoelectric elements are controlled with an a.c. voltage having a d.c. component. Likewise a recessed vibrating surface is possible due to a control of the corresponding piezoelectric elements with an a.c. voltage having a d.c. component, which now has the opposite sign.

BRIEF DESCRIPTION OF THE DRAWINGS

The present invention is described below with reference to the accompanying figures on the basis of exemplary embodiments. In the drawing, identical reference numerals denote identical elements or those having the same function. In the drawings:

FIG. 3 shows a single piezoelectric element having electrodes of a touchscreen according to FIG. 2a;

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
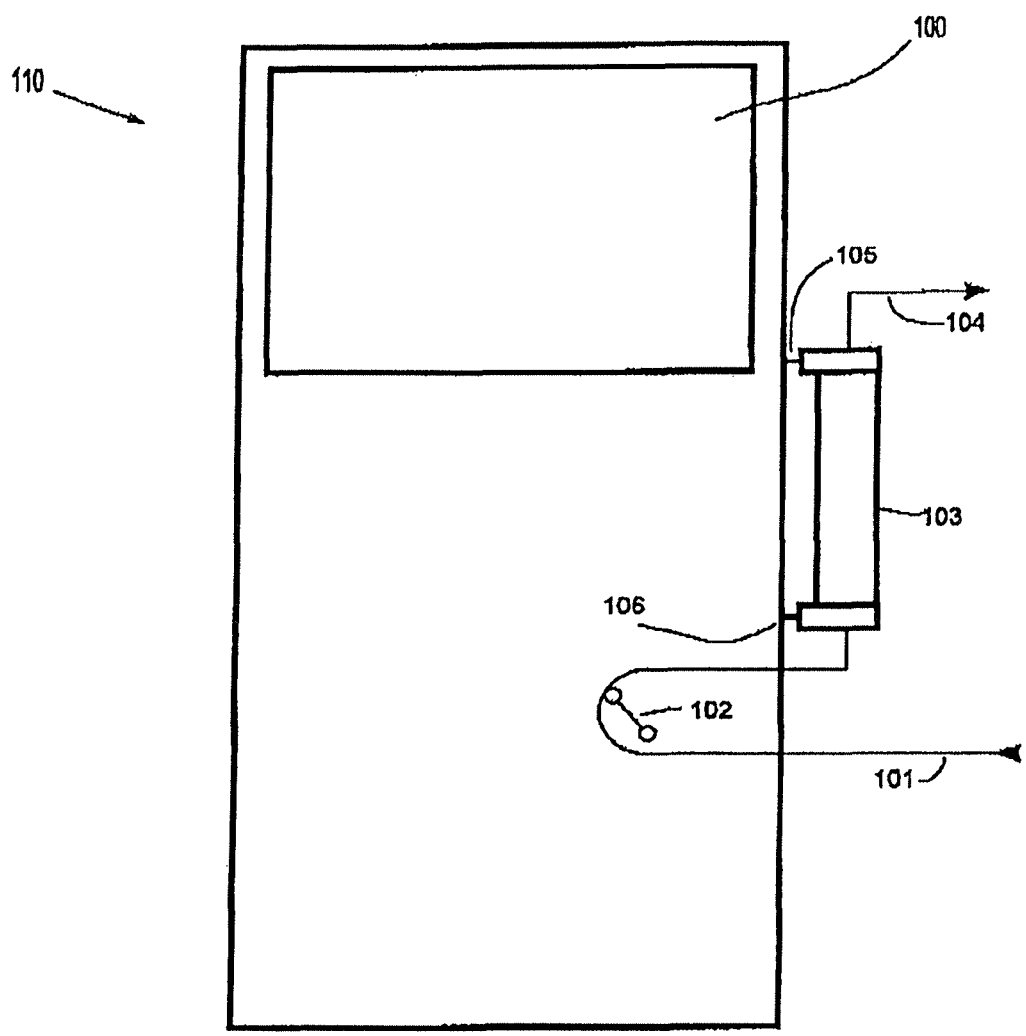
FIG. 1 shows an embodiment of an inventive technical medical device, which is embodied as a dialysis machine.

FIG. 1 shows schematically an embodiment of an inventive technical medical device 110 as a dialysis machine having a touchscreen display with tactile feedback 100. The dialysis machine 110 shows parts of an extracorporeal blood circulation with an arterial blood line 101, which carries the blood of a patient (not shown). The blood pump 102 conveys the blood through a dialysis filter 103, which is equipped with a semipermeable membrane, providing a semipermeable separation between the extracorporeal blood circulation and the dialysate circuit. The treated blood is returned to the patient through the venous line 104. Dialysate is pumped through the dialysis filter 103 by way of the dialysate lines 105 and 106, passing through the semipermeable membrane of the dialysis filter 103 and resulting in a diffusive mass exchange with the patient's blood. If a pressure gradient is additionally built up from the blood side of the dialysis filter to the dialysate side of the patient, plasma water is expressed from the blood into the dialysate. The water content of the patient's blood can thus be reduced. The dialysate is prepared in the hemodialysis machine 110 and is discarded after use.

The dialysis machine in FIG. 1 is designed as a hemodialysis machine. Without restriction, the device and the methods according to the invention can be used with all technical medical devices with which information and operator input can be displaced on a touchscreen display. This also includes explicitly and nonexclusively blood treatment devices, such as devices for automatic peritoneal dialysis as well as devices for hemofiltration, hemo-diafiltration, plasmapheresis or similar methods.

Within the context a dialysis treatment, extensive operator input must usually be made into a dialysis machine and/or information, for example, the selected dialysis method or information about the patient or the treatment course is also to be displayed. An important safety feature of a dialysis treatment is that the operating input functions reliably and unambiguously at all times. Faulty operation or failure of the operating option can have serious consequences for the safety and health of the patient if they are not noticed.

The operating input becomes much more reliable and more convenient in the manner described here due to the inventive use of a touchscreen having tactile feedback in dialysis machines.

The possibilities of operating the operating inputs in the event of failure of the finger pressure sensor of the touchscreen have so far been limited to mechanical switches or operating options, which are on the machine but not on the touchscreen. This may have a deleterious effect on the treatment because the full functionality of the touchscreen cannot be simulated by mechanical switches in a redundant manner, so that a very restricted operability is made possible at any rate.

An alternative method of performing operator inputs which is flexible and redundant in addition to the fingerprint sensor of the touchscreen is created by the device and the methods according to the invention. With a suitable design of the device, operability is not impaired even in the event of a defect in the finger pressure sensor of the touchscreen, and treatment may be continued as scheduled.

Whereas treatment with a conventional technical medical device should be terminated or interrupted for safety reasons in the event of a defect in the finger pressure sensor of the touchscreen, through the present invention the treatment can be continued and terminated as scheduled, which means a significant improvement in the convenience, safety and therapeutic effect of the treatment.

In addition, the present invention offers the option of checking the operator input for whether it is intentional or unintentional, for example, due to unintentional touch in which the force with which pressure is applied to the operating surface is analyzed. Operating safety and reliability are increased and erroneous operating input is prevented in this way.

Through the present invention, the convenience of data input is increased significantly, in that it is possible to impart tactile properties to parts of or the entire touchscreen. It is thus possible to signal to the operator through tactile feedback whether the operating surface which he has just touched is suitable for input, for example, by elevating this operating surface in comparison with the surrounding surface. Faulty operation or input that does not lead to a change in the treatment for safety reasons can also be signaled in a tactile manner in this way, which is more easily noticed by the operator than is the case with just a visual and/or acoustic warning. Thus the operating safety of a technical medical device is further increased through the present invention.

In addition, the present invention offers the possibility of multitouch functionality in the manner already described, i.e., recognizing multiple touches at the same time in different positions on the touchscreen. It is possible in this way to implement convenience features, for example, enlarging displays on the touchscreen or input of value intervals on a value scale through appropriate movements of the fingers. This significantly increases the convenience of data entry and the quality of the display.

Figure 2A:
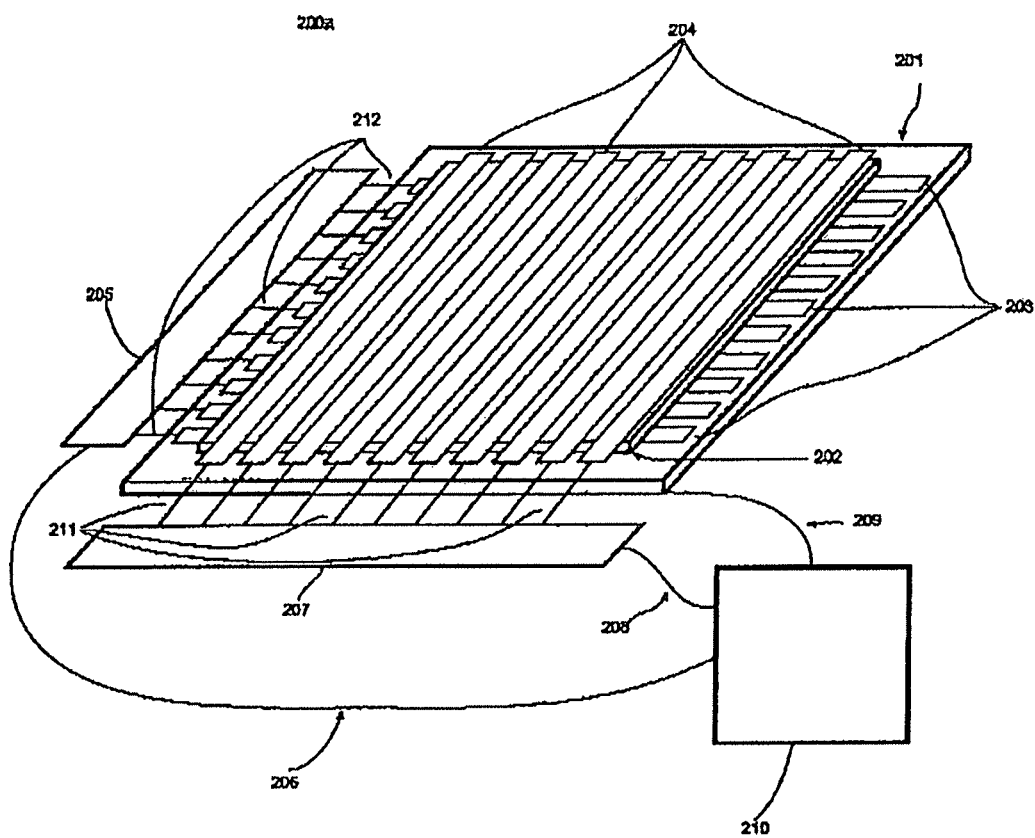
FIG. 2a shows the design of a touchscreen having piezoelectric elements and a symbolic control as a first embodiment of a touchscreen of an inventive technical medical device, as shown in FIG. 1, for example.

FIG. 2a shows an embodiment of a touchscreen 200a with tactile feedback for an inventive technical medical device. A conventional touchscreen display 201, such as that known from the state of the art, is preferably designed in capacitive touchscreen technology.

An arrangement of four electrodes 203 running horizontally, a piezoelectric layer 202 and the electrodes 204 running vertically is arranged here above the display 201.

Horizontal and vertical electrodes may be supplied with a voltage individually and independently of one another via the two control devices 205 and 207 and/or the voltage of the electrodes may be read out. For this purpose, the electrodes 204 are connected to the first control device 207 via the conducting connections 211 and the electrodes 203 are connected to the second control device 205 via the conducting connections 212.

For reasons of simplicity, FIG. 2a shows only a few electrodes. In practice the electrode width may be much smaller, for example, 0.1 mm or less. This increases the number of electrodes and thus increases the resolution of the piezoelectric layer 202.

Both the touchscreen and the horizontal and vertical electrodes are controlled and/or read out via a third control device 210. For this purpose, the third control device 210 is connected to the touchscreen 201 and to the two control devices 205 and 207 via the control and readout lines 206, 208 and 209. The control and readout devices 206, 208 and 209 are usually embodied as a databus and consist of a plurality of signal-carrying lines but may also be individual lines.

A piezoelectric element is formed by an intersection of a vertical electrode 204 with a horizontal electrode 203 with the part of the piezoelectric layer 202 situated between the intersection areas.

If this piezoelectric element is to be controlled, the corresponding electrodes must receive a voltage. The voltage difference of the individual voltages of the electrodes is the control voltage for this piezoelectric element. Depending on the polarity of this voltage difference, the piezoelectric element thereby controlled becomes longer or shorter in the direction of the two electrodes.

The piezoelectric elements cannot be controlled or read out individually at the same time in the embodiment shown in FIG. 2a. Nevertheless a row of neighboring piezoelectric elements can be controlled in the same way to generate an increased operating field, for example.

If the piezoelectric elements are used as force sensors, it is advantageous if individual rows of piezoelectric elements are queried consecutively in rapid sequence. Thus for a period of time t, the voltage between one of the electrodes 203 and all electrodes 204 can be determined by the control devices 205, 207 and 210 in order to then determine the voltage between a neighboring electrode 203 and all electrodes 204 in the same way. In this way, the voltages between all electrodes 203 and all electrodes 204 are subsequently determined consecutively. This process is repeated continuously and allows quasi-continuous monitoring of all piezoelectric elements for the application of force by the pressure of a finger with a sufficiently small period of time t. The period of time t is sufficiently small if the query of all piezoelectric elements takes place more rapidly than possible movements of the finger of the user.

Figure 2B:
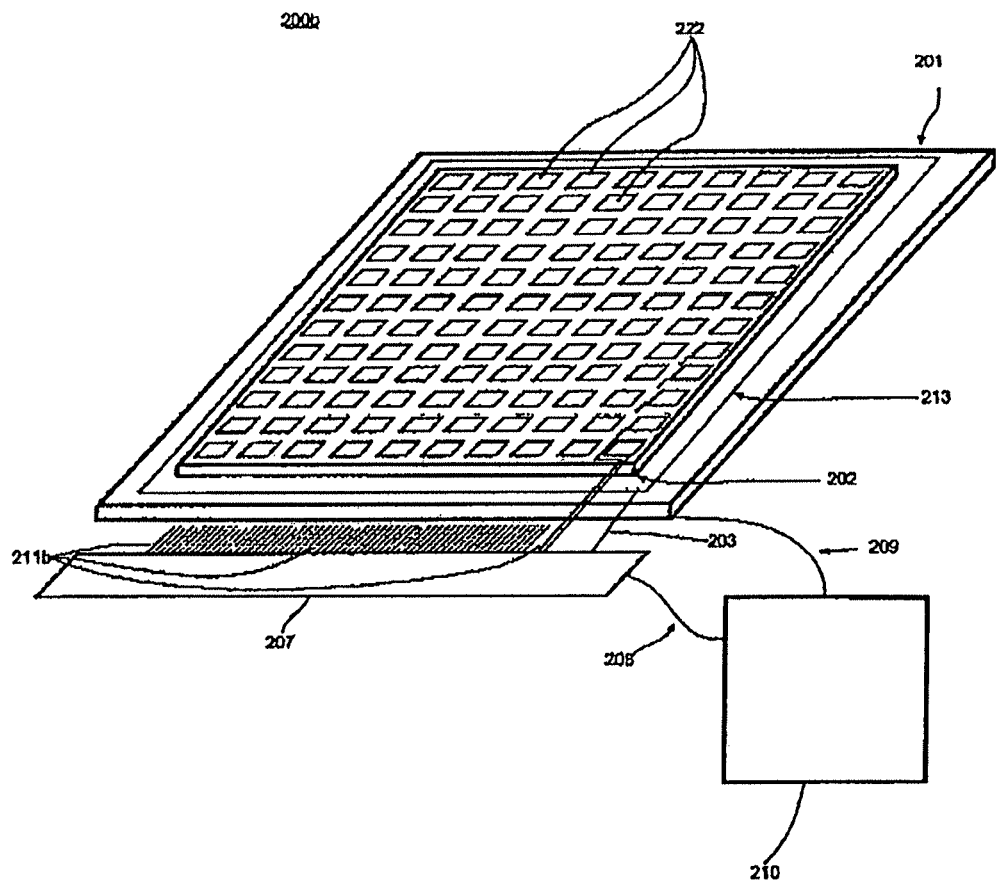
FIG. 2b shows an alternative design of a touchscreen having a plurality of piezoelectric elements and a symbolic control as a second embodiment of a touchscreen of an inventive technical medical device, for example, according to FIG. 1.
Figure 2C:
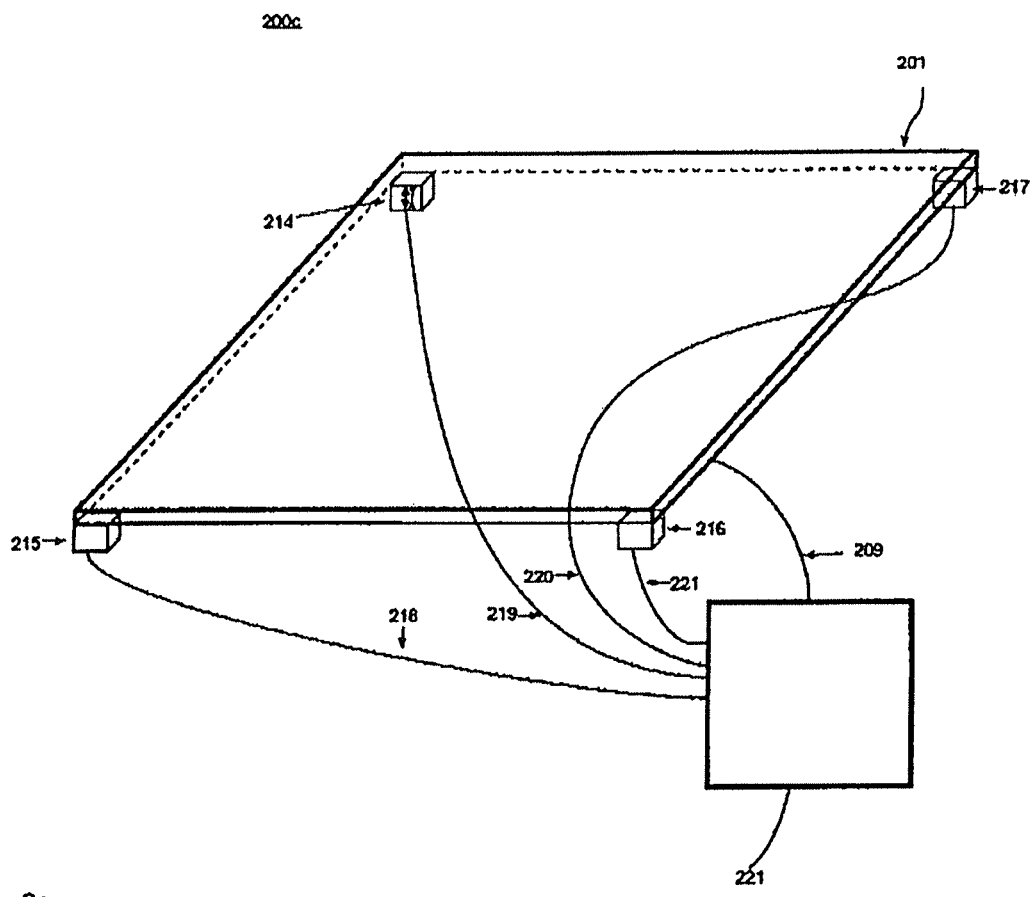
FIG. 2c shows another alternative design of a touchscreen having actuator-type support as the third embodiment of a touchscreen of an inventive technical medical device, as shown according to FIG. 1.

Not shown in the figures is an electrically insulating film above the device 100a, 100b (FIG. 2b) and 100c (FIG. 2c). This film is preferably thin and elastic. In addition to the property of electrically insulating the touchscreen toward the top with tactile feedback, such a film also offers a smooth hygienic surface.

FIG. 2b shows an alternative embodiment of a touchscreen 200b with tactile feedback for an inventive technical medical device. A conventional touchscreen display 201 such as that known from the state of the art is preferably embodied in capacitive touchscreen technology.

A flat, light-permeable electrode 213 is arranged above the touchscreen display 201. It forms a shared electrode for all the piezoelectric elements, which are formed by the piezoelectric layer 202 and the plurality of electrodes 222 (square in this case) on the top side of the piezoelectric layer. Each of the electrodes on the surface is electrically connected by an individual line 211b to the control device 207 (for the sake of simplicity, only the connections to two piezoelectric elements are shown here, but the remaining connections are indicated by broken lines); likewise the shared electrode 213 by the control line 203.

The control lines and readout lines 208 and 209 are usually embodied as a databus and consist of a plurality of signal-carrying lines but may also be individual lines.

The control device 210 receives signals from the first control device 207 and sends signals to the control device 207 via the control and readout line 208. The touchscreen 201 is connected to the control device 210 via the control and readout lines 209.

In the embodiment shown in FIG. 2b, each piezoelectric element may advantageously be controlled and queried individually and simultaneously with all the other piezoelectric elements.

Another embodiment of a touchscreen 100c with tactile feedback is shown in FIG. 2c.

A conventional touchscreen display 201, such as that known in the state of the art, is preferably embodied here in capacitive touchscreen technology.

In this embodiment, the touchscreen display 201 is connected in a force-locked manner to four piezoelectric elements 214, 215, 216 and 217 at the corners. The piezoelectric elements here operate as actuators and force sensors. The piezoelectric elements are controlled via the signal lines 218, 219, 220 and 221 by way of the control device 221 and queried. By the control of the piezoelectric elements, the entire display can move in the direction of the arrows shown in piezoelectric element 214.

In the type of embodiment shown in FIG. 2c, instead of providing partial areas of the touchscreen 201 to be occupied by tactile properties, only the entire area of the touchscreen may have such properties. It is nevertheless possible to provide a user with tactile feedback having local resolution.

To do so, when the pressure of a finger is detected by the finger pressure sensor of the touchscreen and by the control unit 221, a decision is made immediately as to whether an elevation (or a recess and/or vibration) should be perceived at the location where the finger touches the touchscreen. If this is the case (the operator is depressing an operating area as shown, for example), the piezoelectric elements 214 to 217 are controlled in such a way that the entire display is elevated. If the operating finger then moves to a location to which a recess, a vibration or a location within the normal user plane is assigned, the piezoelectric elements 214 to 217 are controlled in such a way that the entire display moves accordingly. Since the user normally uses only one finger for input of information, this gives the impression of tactile feedback in the form of tactile properties of the touchscreen having position resolution.

This embodiment may also be used for detecting the pressure of a finger. If an operator depresses a location on the display, the force is distributed in inverse proportion to the distance from the individual piezoelectric elements 214 to 217 on the elements or the display. If the electrical voltages of the individual piezoelectric elements triggered by the application of force are measured and analyzed by the control unit 221, the position of the finger pressure can thus be determined.

Figure 3:
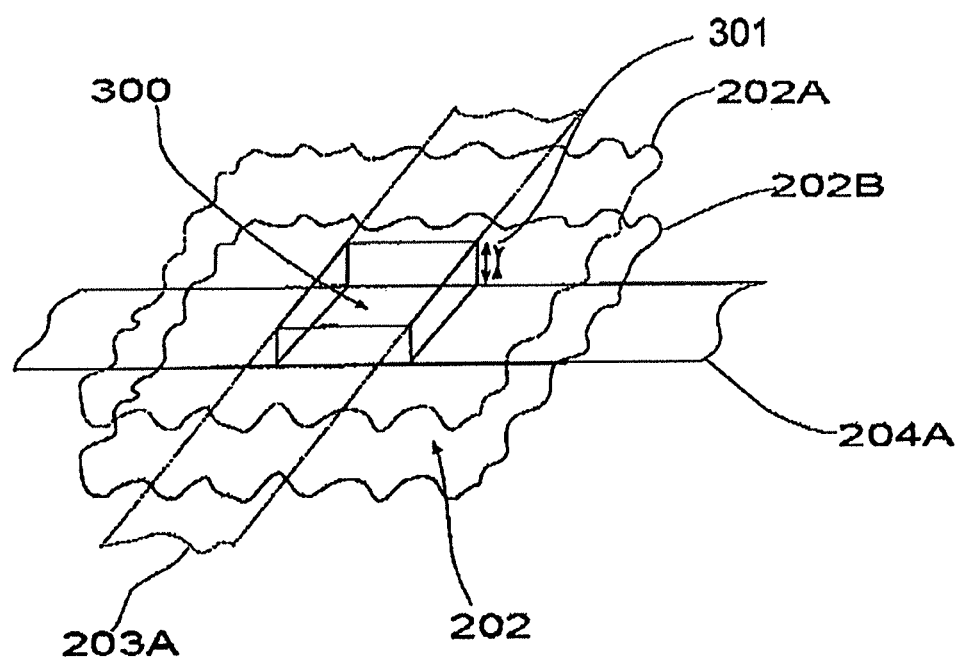

FIG. 3 shows an individual piezoelectric element 300 for better illustration, this piezoelectric element being formed by the intersection of the electrode 203A with the electrode 204A and the part of the piezoelectric layer 202 situated between the intersecting surfaces by analogy with FIG. 2a. The bordering area 202A shown here with dotted lines represents a detail of the upper bordering area of the piezoelectric layer 202, while the solid bordering area 202B represents a detail of the lower bordering area of the piezoelectric layer 202.

The upper electrode 203A, which is shown with dotted lines, runs above 202A and touches this interface, so that electrical contact is established. Similarly, the lower electrode 204A runs below 202B and touches this interface.

A differential voltage may be applied to piezoelectric element 300 via the two electrodes 202A and 203A and a voltage drop across the piezoelectric element 300 which can also be read out, for example, with deformation of the piezoelectric element 300 caused by external pressure.

The piezoelectric element 300 is also deformed due to a differential voltage applied via the two electrodes 202A and 203A in the direction of the electrodes 202A and 203A, as indicated by the two arrows 201 in FIG. 3.

Figure 4:
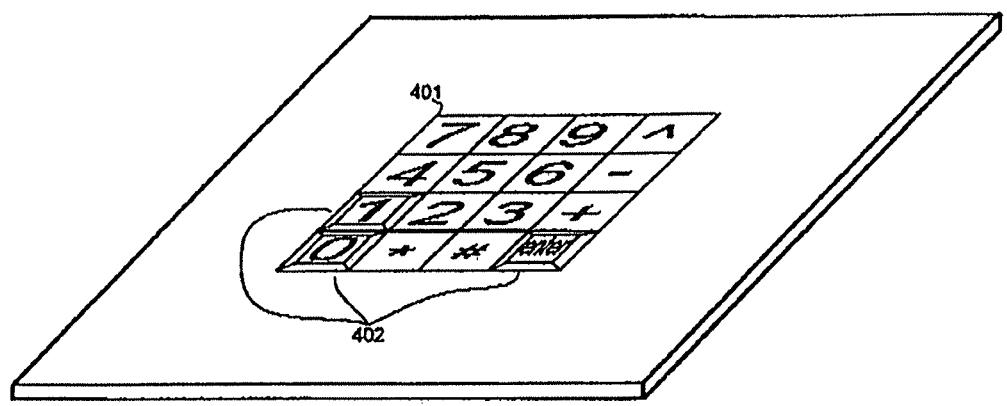
FIG. 4 shows an example of a display of a touchscreen, for example, according to FIG. 2a on an inventive technical medical device having additional tactile information.

FIG. 4 shows the touchscreen with tactile feedback 100 with an input field 401 as shown here. The input field 401 is embodied, for example, as a 10-key keypad with a few function keys, but it will be clear to those skilled in the art that any representation is likewise possible.

The operating fields 402 ("0," "1" and "enter") are shown in FIG. 4 as being elevated. This may characterize an allowed input which can be detected as a tactile sensation, for example. Likewise operating fields may be characterized in a manner already described by a tangible depression in comparison with the surrounding areas, by a vibration or a change in the roughness perceived.

Due to the special tactile properties of partial areas of the touchscreen, represented in FIG. 4 as an elevation of the operating fields with the assigned numbers "0," "1" and "enter," the convenience of input for the operator is increased on the one hand, while on the other hand the safety of operation is also increased because improbable inputs are characterized by the additional feature of the tactile property.

With the help of this invention, it is possible to design technical medical devices which are equipped with a touchscreen to be safer and more convenient. The present invention is not limited to the embodiments described above; these serve only the purpose of illustration. It is self-evident to those skilled in the art to use features of the invention to design additional embodiments.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for display and input, of information on a technical medical device having at least one touchscreen, said method comprising:
    determining with two redundant sensors a position of a finger pressure on the touchscreen, at least one of the two redundant sensors including a plurality of piezoelectric elements;
    detecting with a control unit signals of the two redundant sensors that determine the position of the finger pressure on the touchscreen;
    determining with the control unit whether there has been an unintentional finger pressure on the touchscreen when the signal of at least one of the two redundant sensors is too low;
    determining whether a visual display of the touchscreen is functioning; and
    if the visual display of the touchscreen is determined to not be functioning, controlling the plurality of piezoelectric elements such that partial areas of the touchscreen have different tactile properties.

2. The method according to claim 1, wherein the plurality of piezoelectric elements can be controlled to undergo a deformation.

3. The method according to claim 2, wherein the deformation is at least one of a recess, an elevation, and a vibration perpendicular to a surface of the touchscreen.

4. The method according to claim 1, wherein the control unit is configured to at least one of (i) apply an electrical voltage to each of the plurality of piezoelectric elements and (ii) measure an electrical voltage drop across each of the plurality of piezoelectric elements.

5. The method according to claim 4, wherein the control unit is configured to determine the positions and the application of force of any finger pressure on the touchscreen from the measured voltages of each of the plurality of piezoelectric elements.

6. The method according to claim 1, wherein the control unit concludes that there is a fault case when the signal of only one of the two redundant sensors is detected.

7. The method according to claim 1, wherein the finger pressure on one of the partial areas of the touchscreen triggers a predefined action of the technical medical device.

8. The method according to claim 1, wherein the control unit analyzes the signals of the two redundant sensors so as to ascertain the positions of multiple fingers simultaneously depressing the touchscreen.

9. A method of displaying and inputting information on a medical device having at least one touchscreen, said method comprising:
    determining a position of a finger pressure on the touchscreen with a first and a second redundant sensor, with at least one of the first and the second redundant sensors including a plurality of piezoelectric elements;
    determining whether a visual display of the touchscreen is functioning; and
    if the visual display of the touchscreen is determined to not be functioning, controlling the plurality of piezoelectric elements such that partial areas of the touchscreen have different tactile properties.

10. The method according to claim 9, wherein the finger pressure on one of the partial areas of the touchscreen triggers a predefined action of the medical device.

11. The method according to claim 9, further comprising a step of detecting with a control unit signals of the first and second redundant sensors for determining the position of the finder pressure on the touchscreen.

12. The method according to claim 11, wherein the control unit concludes that there has been an unintentional finger pressure when the signal of at least one of the first and second redundant sensors is too low.

13. A medical device having at least one touchscreen for displaying and inputting information, said device comprising:
    a first and a second redundant sensor for determining a position of a finger pressure on the touchscreen, with at least one of the first and the second redundant sensors including a plurality of piezoelectric elements,
    the device being configured (i) to determine whether a visual display of the touchscreen is functioning, and (ii) if the visual display of the touchscreen is determined to not be functioning, control the plurality of piezoelectric elements such that partial areas of the touchscreen have different tactile properties.

14. The medical device according to claim 13, wherein the medical device is a blood treatment device configured for hemodialysis, hemofiltration, hemodiafiltration, plasmapheresis, or automatic peritoneal dialysis.

15. The medical device according to claim 13, wherein the finger pressure on one of the partial areas of the touchscreen triggers a predefined action, of the medical device.

16. The medical device according to claim 13, wherein the plurality of piezoelectric elements are controlled to undergo a deformation that is at least one of a recess, an elevation, and a vibration perpendicular to a surface of the touchscreen.

17. The medical device according to claim 13, further comprising a control unit configured to at least one of (i) apply an electrical voltage to each of the plurality of piezoelectric elements and (ii) measure an electrical voltage drop across each of the plurality of piezoelectric elements.

18. The medical device according to claim 13, wherein the control unit is configured to at least one of (i) communicate a presence of an operational defect to an operator and (ii) communicate the presence of the operational defect to another control unit.

19. The medical device according to claim 18, wherein the communication is at least one of a visual, a tactile, and an acoustic signal, and a control signal.

* * * * *